United States Patent
Habets

(10) Patent No.: US 7,141,151 B2
(45) Date of Patent: Nov. 28, 2006

(54) MEASUREMENT DEVICE FOR DETERMINING OXYGEN ACTIVITY IN MOLTEN METAL OR SLAG

(75) Inventor: Danny Habets, Genk (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 145 days.

(21) Appl. No.: 10/795,106

(22) Filed: Mar. 5, 2004

(65) Prior Publication Data

US 2004/0173473 A1 Sep. 9, 2004

(30) Foreign Application Priority Data

Mar. 7, 2003 (DE) ................... 103 10 387

(51) Int. Cl.
*G01N 27/411* (2006.01)
(52) U.S. Cl. .............. 204/422; 204/424; 205/790
(58) Field of Classification Search ........... 204/422; 205/790
See application file for complete search history.

(56) References Cited

U.S. PATENT DOCUMENTS

| 3,578,578 | A | * | 5/1971 | Von Krusenstierna ...... 204/422 |
| 5,332,449 | A | | 7/1994 | Verstreken et al. |
| 6,855,238 | B1 | * | 2/2005 | Knevels et al. ............. 204/422 |

FOREIGN PATENT DOCUMENTS

DE 26 00 103 B1 4/1977

(Continued)

OTHER PUBLICATIONS

Oktay, E. and Fruehan, R. J., "On the hot metal desulfurization", Steel Research, vol. 66 No. 3, 1995, pp. 93-95.*

(Continued)

*Primary Examiner*—Nam Nguyen
*Assistant Examiner*—Anthony Fick
(74) *Attorney, Agent, or Firm*—Akin Gump Strauss Hauer & Feld, LLP

(57) ABSTRACT

A measurement device is provided for determining the oxygen activity in molten metal or slag with a measurement head, which is arranged at one end of a carrier tube and on which an electrochemical measurement cell is arranged. The electrochemical measurement cell has a solid electrolyte tube, which is closed at one end and which contains a reference material and an electrode at its closed end. The electrode projects from the opposite end of the solid electrolyte tube. The outer surface of the solid electrolyte tube has a coating of a mixture of calcium zirconate with a fluoride. The measurement device can be used for calculating the sulfur, silicon and/or carbon content of the molten metal or slag from reaction of the sulfur with the calcium zirconate, which releases oxygen, and measurement of the resulting change in oxygen activity of the melt or slag at the outer surface of the solid electrolyte tube.

19 Claims, 2 Drawing Sheets

FOREIGN PATENT DOCUMENTS

| | | |
|---|---|---|
| DE | 26 00 103 C2 | 11/1978 |
| DE | 28 10 134 A1 | 9/1979 |
| DE | 31 52 318 C2 | 11/1986 |
| DE | 41 35 510 C2 | 2/1994 |
| DE | 195 31 661 C2 | 8/2002 |
| EP | 0 295 112 A2 | 6/1988 |
| EP | 0295 112 A2 * | 12/1988 |
| JP | 60-52763 A | 3/1985 |

OTHER PUBLICATIONS

Kequin Huang et al., "A new electrochemical sensor for rapid determination of silicon content in carbon saturated iron", *Solid State Ionics*, vol. 53-56, pp. 24-29, (1992).

M. Iwase et al., "Some Recent Developments in Solid State Galvanic Sensor", *Proceedings of the Symposium on High Temperature Materials Chemistry*, vol. 82-1, pp. 431-455, (1982).

Enver Oktay et al., "On the hot metal desulfurization", *Steel Research*, vol. 66, No. 3, pp. 93-95, (1995).

* cited by examiner

MEASUREMENT DEVICE FOR DETERMINING OXYGEN ACTIVITY IN MOLTEN METAL OR SLAG

BACKGROUND OF THE INVENTION

The invention relates to a measurement device for determining the oxygen activity in molten metal or slag with a measurement head, which is arranged at one end of a carrier tube and on which an electrochemical measurement cell is arranged. The electrochemical measurement cell has a solid electrolyte tube, which is closed on one end and which contains a reference material and an electrode at its closed end, wherein the electrode projects out of the opposite end of the solid electrolyte tube. In addition, the invention relates to a solid electrolyte tube for an electrochemical measurement cell.

Such measurement devices are known, for example, from German Patent DE 31 52 318 C2. The sensor described in this document is used to measure the concentration of oxygen in molten metal. Similar measurement devices are also known from U.S. Pat. No. 3,578,578, German published patent application DE 28 10 134 A1, or German Patent DE 26 00 103 C2.

BRIEF SUMMARY OF THE INVENTION

In addition to oxygen, there is the need to measure other materials contained in molten metals. Therefore, the invention is based on the object of providing a simple measurement device and also a corresponding solid electrolyte tube, with which, in addition to the oxygen content, the concentration of other elements can also be determined.

The object is achieved in that the outer surface of the solid electrolyte tube has a coating of a mixture of calcium zirconate with a fluoride. It has been shown that this coating allows the determination of the concentration, for example, of sulfur, silicon, or carbon in melts. The effect can be explained in that the sulfur, for example, found in the liquid metal reacts with the CaO from the calcium zirconate, producing oxygen as a reaction product, and the change of the oxygen activity at the surface of the solid electrolyte is measured and correlated with the sulfur. The measurement device can be used in molten metal or slag, especially in steel or iron melts, for measuring the concentration of sulfur, silicon, or carbon. A quick measurement is obtained thereby. It is advantageous if the measurement device has, in addition to the electrochemical measurement cell, a temperature sensor, for example a thermocouple, so that the temperature of the molten metal can also be measured. Silicon is correlated with the sulfur content. Carbon can be calculated from the silicon-carbon thermal equilibrium of the molten metal.

With the measurement device according to the invention, a sample analysis in the laboratory can be avoided, so that considerable savings of time in the production process and consequently an improved and quicker influence of production process can be achieved.

Advantageous embodiments of the invention are given in the below and in the dependent claims. It is expedient that the fluoride be at least one from the group of $CaF_2$, $NaF$, $SrF_2$, $BaF_2$, $MgF_2$. It is advantageous for high measurement sensitivity that the calcium zirconate be stoichiometric. Likewise, it is advantageous that the coating have a thickness of approximately 10–100 μm, especially about 30 μm. Here, a thinner layer is sufficient at higher temperatures of use (for example, before a desulfurization treatment). In this case, the response time is rather short. At lower temperatures of use (for example, after the desulfurization treatment) a thicker coating is required. The response time is then somewhat longer.

The solid electrolyte tube is advantageously stabilized $ZrO_2$. The layer can also only partially cover the outer surface of the solid electrolyte tube, wherein the surface of the tube should be coated at least in the region in which the reference mass is arranged.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
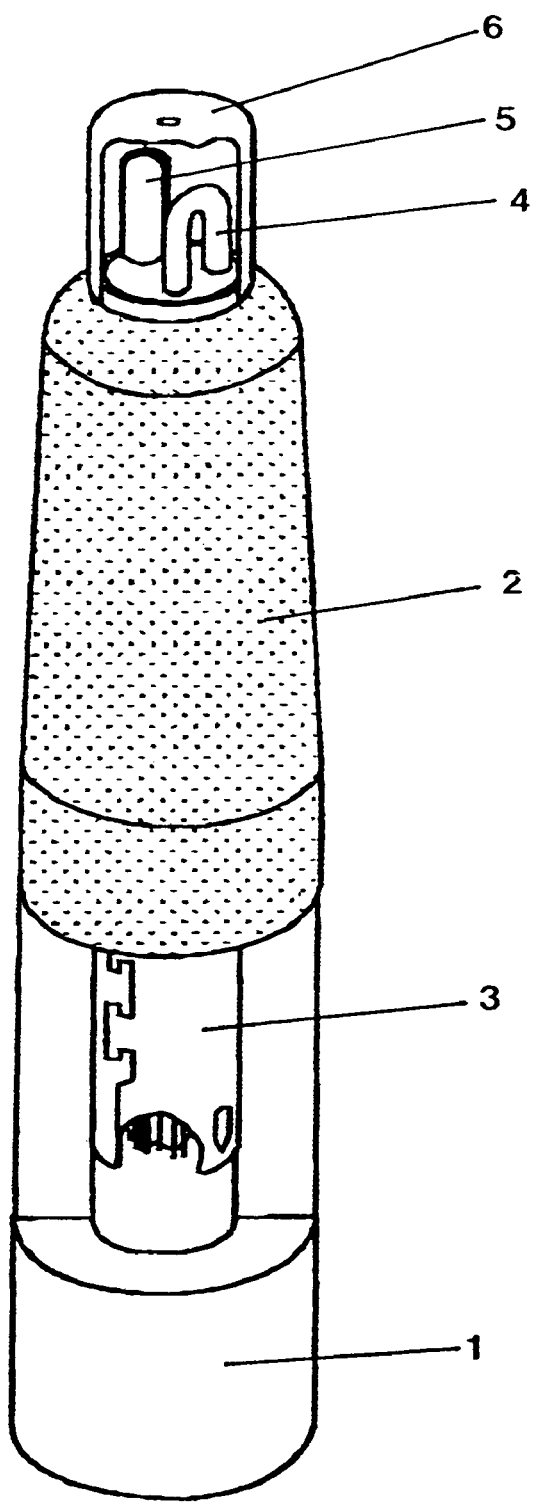
FIG. 1 is front perspective view of a measurement device according to the invention.

The measurement device has a carrier tube 1, in which the measurement head 2 is held, wherein the measurement head 2 connects inside the carrier tube 1 to a supply line to the measurement and evaluation circuits through a contact piece 3. The carrier tube 1 is shown only at its beginning in FIG. 1.

At the immersion end of the measurement head 2, in addition to a thermocouple 4, there is a solid electrolyte tube 5. Thermocouple 4 and solid electrolyte tube 5 are surrounded by a protective cap 6 and are each protected before and during the immersion of the measurement head into the melt, particularly molten iron or steel.

Figure 2:
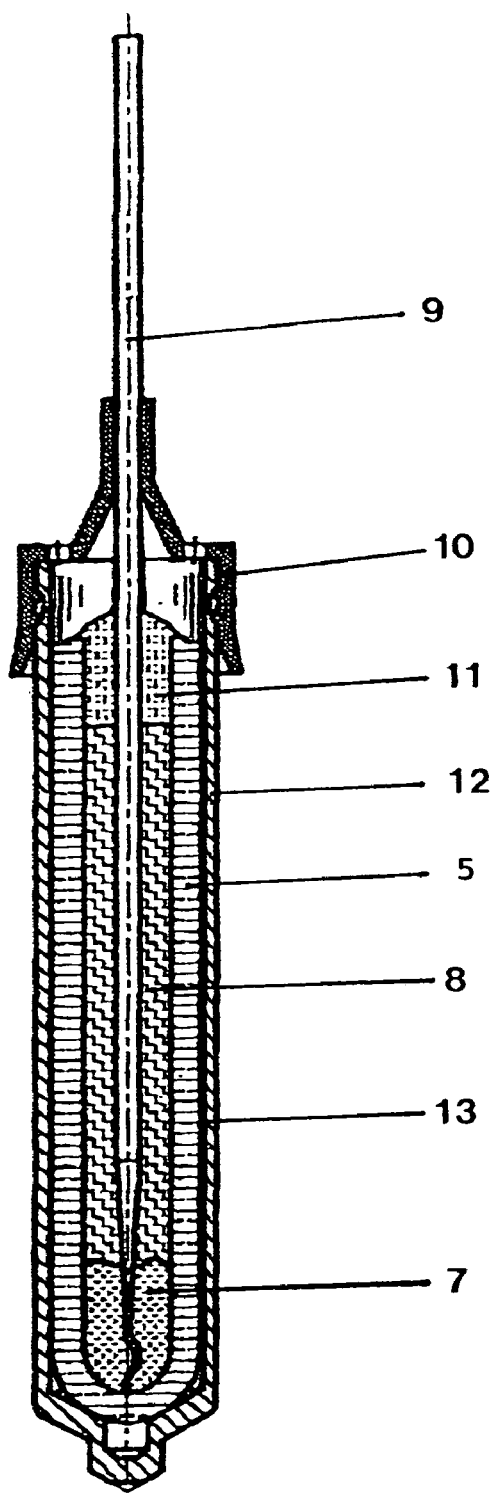
FIG. 2 is a cross sectional view through a solid electrolyte tube used in the measurement device of FIG. 1.

In FIG. 2 the solid electrolyte tube 5 is shown in section. It is produced from stabilized zirconium dioxide and has in its interior a mixture of chromium and chromium dioxide as a reference material 7. The filling material 8 arranged on top of this mixture is aluminum oxide, for example. In the center of the solid electrolyte tube 5 there is arranged a molybdenum rod as electrode 9. The electrode 9 projects from the open end of the solid electrolyte tube 5. This open end is closed by a cap 10, wherein the filling material 8 is held at its upper end by a gas-permeable cement 11. The solid electrolyte tube 5 is surrounded by a steel cap 12, which also protects the tube during the immersion in the molten metal. It then melts and exposes the coating 13 arranged on the solid electrolyte tube 5. The coating is preferably a mixture of calcium zirconate and magnesium fluoride.

In the melt CaO reacts with sulfur with formation of CaS, whereby oxygen is released, whose activity is measured with the aid of the solid electrolyte tube.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A measurement device for determining oxygen activity in a molten metal or slag, comprising a measurement head arranged at one end of a carrier tube and an electrochemical measurement cell arranged on the measurement head, the electrochemical measurement cell having a solid electrolyte tube, which is closed on one end and which contains a reference material and an electrode at the closed end, wherein the electrode projects from an end of the solid electrolyte tube opposite from the closed end, wherein an outer surface of the solid electrolyte tube has a coating of a mixture of calcium zirconate with a fluoride.

2. The measurement device according to claim 1, wherein the fluoride is at least one selected from the group consisting of $CaF_2$, $NaF$, $SrF_2$, $BaF_2$, and $MgF_2$.

3. The measurement device according to claim 1, wherein the calcium zirconate is stoichiometric.

4. The measurement device according to claim 1, wherein the coating has a thickness of approximately 10 to 100 μm.

5. The measurement device according to claim 1, wherein the coating only partially covers the outer surface of the solid electrolyte tube.

6. A method for determining a content of sulfur, silicon, and/or carbon in molten metal or slag, comprising immersing the measurement head of the measurement device of claim 1 into the molten metal or slag, measuring a change in the oxygen activity in the melt or slag with the solid electrolyte tube at its outer surface, and calculating the content of sulfur, silicon and/or carbon from the measurement.

7. The method according to claim 6, wherein the molten metal is steel or iron.

8. The method according to claim 6, wherein the content of sulfur is calculated by correlation with the change in oxygen activity from reaction of sulfur with the calcium zirconate in the coating.

9. The method according to claim 8, wherein the content of silicon is calculated by correlation with the sulfur content.

10. The method according to claim 9, wherein the content of carbon is calculated from a silicon-carbon equilibrium of the molten metal or slag.

11. The measurement device according to claim 1, wherein the fluoride is $MgF_2$.

12. The measurement device according to claim 1, wherein the solid electrolyte tube comprises stabilized $ZrO_2$.

13. A solid electrolyte tube for an electrochemical measurement cell with a closed end, wherein the solid electrolyte tube has on its outer surface a coating of a mixture of calcium zirconate with a fluoride.

14. The solid electrolyte tube according to claim 13, wherein the fluoride is at least one from the group consisting of $CaF_2$, $NaF$, $SrF_2$, $BaF_2$, and $MgF_2$.

15. The solid electrolyte tube according to claim 13, wherein the calcium zirconate is stoichiometric.

16. The solid electrolyte tube according to claim 13, wherein the coating has a thickness of approximately 10 to 100 μm.

17. The solid electrolyte tube according to claim 13, wherein the coating only partially covers the outer surface.

18. The solid electrolyte tube according to claim 13, wherein the fluoride is $MgF_2$.

19. The solid electrolyte tube according to claim 13, wherein the solid electrolyte tube comprises stabilized $ZrO_2$.

* * * * *